United States Patent [19]

Cragoe, Jr. et al.

[11] 4,336,397
[45] Jun. 22, 1982

[54] 2,4-DIOXO-4-SUBSTITUTED-1-BUTANOIC ACID DERIVATIVES USEFUL IN TREATING URINARY TRACT CALCIUM OXALATE LITHIASIS

[75] Inventors: Edward J. Cragoe, Jr., Lansdale, Pa.; Arthur A. Patchett, Westfield, N.J.; Clarence S. Rooney, Worcester, Pa.; Haydn W. R. Williams, Dollard des Ormeaux, Canada

[73] Assignee: Merck & Co., Inc., Rahway, N.J.

[21] Appl. No.: 221,159

[22] Filed: Dec. 29, 1980

[51] Int. Cl.³ .................................. C07C 69/76
[52] U.S. Cl. .............................. 560/51; 562/459; 562/462; 424/308; 260/501.1; 260/501.13; 260/501.15
[58] Field of Search ............. 560/51, 53; 562/459, 562/462, 463; 260/501.1, 501.13, 501.15

[56] References Cited
PUBLICATIONS

Breusch and Keskin, Enzymologia 11, 356–360, (1945).
Fatutta and Balestra, Gazz. Chim ital., 88, 899–909 (1958).

*Primary Examiner*—Paul J. Killos
*Attorney, Agent, or Firm*—Raymond M. Speer; Martin L. Katz

[57] ABSTRACT

2,4-Dioxo-4-substituted-1-butanoic acid derivatives of the formula:

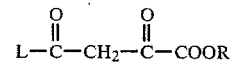

(I)

$$L-\overset{O}{\underset{\|}{C}}-CH_2-\overset{O}{\underset{\|}{C}}-COOR$$

where
R is hydrogen or $C_{1-4}$ alkyl; and
L is a lipophilic group consisting essentially of:

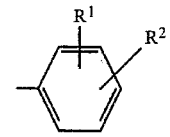

(1)

where
$R^1$ and $R^2$ are each independently selected from the group consisting of (a) hydrogen; (b) $C_{4-12}$ straight or branched chain alkyl; (c) $C_{4-7}$ cycloalkyl; and (d) tetrahydronaphthyl; provided that $R^1$ and $R^2$ may not both be hydrogen; and when one of $R^1$ or $R^2$ is tetrahydronaphthyl, the other must be some other substituent; and that positions 2 and 6 of the substituted phenyl moiety may not be substituted; and

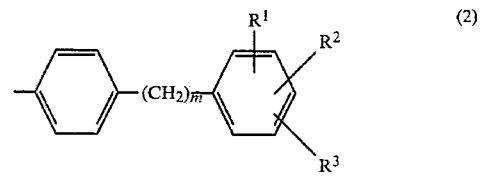

(2)

where $R^1$, and $R^2$ have the same meaning as above except tetrahydronaphthyl;
$R^3$ is bromine, chlorine, or fluorine;
m is 0 to 3;
or a pharmaceutically acceptable salt thereof.

8 Claims, No Drawings

2,4-DIOXO-4-SUBSTITUTED-1-BUTANOIC ACID DERIVATIVES USEFUL IN TREATING URINARY TRACT CALCIUM OXALATE LITHIASIS

BACKGROUND OF THE INVENTION

1. Field of the Invention

The present invention is concerned with novel 2,4-dioxo-4-substituted-1-butanoic acid compounds useful in treating urinary tract, especially renal calcium oxalate lithiasis. The novel compounds of the present invention act as potent inhibitors of the enzyme glycolate oxidase.

The present invention is also concerned with a method of treating or preventing the formation of calcium oxalate urinary tract lithiasis, especially kidney or bladder stones, as well as pharmaceutical compositions useful in such a method, containing the novel 2,4-dioxo-4-substituted-1-butanoic acid compounds as active ingredient.

Close to 70% of kidney stones are composed partially or predominantly of calcium oxalate; yet there is no satisfactory drug specific for the treatment of calcium oxalate urinary tract lithiasis, nor for prophylactic use by people prone to recurrent attacks of this disease.

Calcium oxalate lithiasis, formation of stony concretions composed partially or predominantly of calcium oxalate, may occur at different points in the urinary tract, and is especially a problem in the kidney and in the bladder.

Approximately 70% of all renal calculi contain oxalate as the main anionic component of the matrix. In many, but not all patients, the condition is associated with a higher than normal level of metabolically produced oxalate.

Common procedures for treatment of renal lithiasis due to calcium oxalate consist of surgical removal of stones, or control of the diet to restrict intake of calcium and/or oxalate combined with ingestion of large quantities of water to dilute the urine. Attempts at chemotherapy have included the administration of magnesium oxide, orthophosphate, cellulose phosphate, isocarboxazide, thiazide diuretics, allopurinol and succinimide. Limited success has been realized so far by these drug approaches. No drug which specifically inhibits the biosynthetic formation of oxalic acid is available for the treatment of calcium oxalate urinary tract, especially renal lithiasis.

The major precursor of oxalate is glyoxylate. Thus, approaches to the reduction of the biosynthetic output of oxalic acid focus on (a.) the prevention of the conversion of glyoxylate to oxalate, and/or (b.) restriction of the production of glyoxylate from its precursors. A major pathway for the biosynthesis of oxalate can be represented as follows:

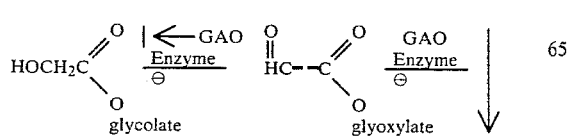

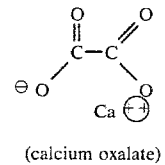

(calcium oxalate)

The same enzyme glycolate oxidase participates both in the biosynthesis of glyoxylate and, in its oxidation to oxalate. An inhibitor of the enzyme will act to block at two key points in the chain of reactions contributing to the production of oxalic acid. As a direct consequence of reducing oxalic acid levels in the urine with the compounds of this invention, the formation of oxalate calculi will be reduced or prevented in individuals whose urinary oxalate is primarily of metabolic origin.

The novel 2,4-dioxo-4-substituted-1-butanoic acid compounds described herein are potent inhibitors of glycolate oxidase and are thus useful in the treatment and prevention of urinary tract lithiasis, especially renal disease due to calcium oxalate stone formation in the kidney. As inhibitors of glycolate oxidase, the novel compounds of the present invention may also be useful in the treatment of primary hyperoxaluria. In the genetically inherited diseases designated hyperoxaluria types I and II, large quantities of oxalic acid are produced metabolically. Crystallization of calcium oxalate, occurring not only in the kidney and bladder, but in other tissues as well, frequently results in early death. The novel compounds of this invention may prove of value in the treatment of these rare but serious disease states.

2. Brief Description of the Prior Art

Glycolic acid oxidase inhibitors are described in U.S. Pat. Nos. 4,178,386; 4,207,329; and 4,233,452. Diketo fatty acids are described in Breusch and Keskin, Enzymologia 11, 356–60 (1945). 4-Aryl-3-bromo-2,4-dioxobutyrate esters are described in Andreichikov et al. U.S.S.R. Pat. No. 466,208. Ethyl p-phenylbenzoylpyruvate is described in Fatutta and Balestra, Gazz. Chim ital., 88, 899–909 (1958). However, none of the compounds described in any of the above would suggest the novel 2,4-dioxo-4-substituted-1-butanoic acid compounds of the present invention.

SUMMARY OF THE INVENTION

The novel 2,4-dioxo-4-substituted-1-butanoic acid compounds of the present invention which are useful in treating and preventing urinary tract calcium oxalate lithiasis, especially the formation of calcium oxalate kidney or bladder stones, can be shown by the following formula:

where
R is hydrogen or $C_{1-4}$ alkyl; and
L is a lipophilic group consisting essentially of:

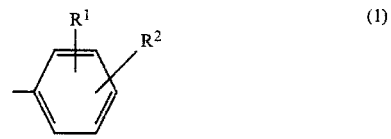

where
R[1] and R[2] are each independently selected from the group consisting of (a) hydrogen; (b) $C_{4-12}$ straight or branched chain alkyl; (c) $C_{4-7}$ cycloalkyl; and (d) tetrahydronaphthyl; provided that R[1] and R[2] may not both be hydrogen; and when one of R[1] and R[2] is tetrahydronaphthyl, the other must be some other substituent; and that positions 2 and 6 of the substituted phenyl moiety may not be substituted; and

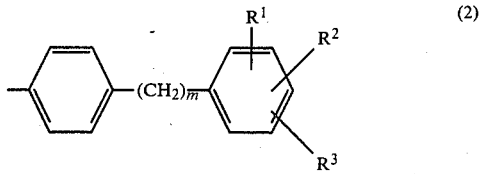

where R[1], and R[2] have the same meaning as above except tetrahydronaphthyl;
R[3] is bromine, chlorine, or fluorine;
m is 0 to 3;
or a pharmaceutically acceptable salt thereof.

The enolic tautomer forms of the novel compounds of Formula I are also understood to be included within the scope of the present invention. These enol forms may be shown by the following formulas:

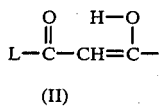      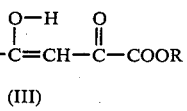

(II)          (III)

Particularly preferred compounds of Formula I are the following:
4-[(1,1'-biphenyl)-4-yl]-2,4-dioxo-1-butanoic acid;
4-(4-cyclohexylphenyl)-2,4-dioxo-1-butanoic acid;
2,4-dioxo-4-(4-nonylphenyl)-1-butanoic acid;
4-[(4'-bromo-1,1-diphenyl)-4-yl]-2,4-dioxo-1-butanoic acid;
4-[4-(1,2,3,4-tetrahydro-1-naphthalenyl)phenyl]-2,4-dioxo-1-butanoic acid;
4-[4-(3,4-dichlorophenylmethyl)phenyl]-2,4-dioxo-1-butanoic acid.

Included within the scope of the present invention are the pharmaceutically acceptable salts of the 2,4-dioxo-4-substituted-1-butanoic acid compounds.

Formula I compounds are organic acids with a pKa in the range of 2 to 5 and thus can be used in the form of salts derived from inorganic or organic bases. Included among such salts are the following: metallic cations such as aluminum, calcium, lithium, magnesium, potassium, sodium, and zinc; and organic cations such as choline, diethanolammonium, n-methylglucammonium, ethanolammonium, diethylammonium, and triethanolammonium. Neutralization can be carried out by a variety of procedures known to the art to be generally useful for the preparation of such salts. The choice of the most suitable procedure will depend on a variety of factors including convenience of operation, economic considerations, and particularly the solubility characteristics of the particular free base, the acid, and the acid addition salt. Water or oil-soluble or dispersible products are thereby obtained.

The Formula I compounds can be administered to patients (both human and animal) having, or being prone, to calcium oxalate kidney or bladder stone disease by formulating them in a composition such as tablet, capsule or elixir for oral administration. Sterile solutions or suspensions can be used for parenteral administration. About 25 to 500 mg of a compound of Formula I or a pharmaceutically acceptable salt is compounded with a pharmaceutically acceptable vehicle, carrier, excipient, binder, preservative, stabilizer, flavor, etc., in a unit dosage form as called for by accepted pharmaceutical practice. The amount of active substance in the composition is such that dosage in the range indicated is obtained. The total daily dose administered to patients having or prone to calcium oxalate kidney or bladder stone disease will be in the 50 mg to 2000 mg range with a preferred daily dose being 100 mg to 1000 mg of active ingredient. It will be realized by those skilled in the art that the dosage range for any particular patient (animal or human) will depend upon the severity of the disease treated, weight of the patient and any other condition which the physician or other person skilled in the art will take account of.

Illustrative of the adjuvants which may be incorporated in tablets, capsules and the like are the following: a binder such as gum tragacanth, acacia, corn starch or gelatin; an excipient such as dicalcium phosphate; a distintegrating agent such as corn starch, potato starch, alginic acid and the like; a lubricant such as magnesium stearate; a sweetening agent such as sucrose, lactose, or saccharin; a flavoring agent such a peppermint, oil of wintergreen or cherry. When the dosage unit form is a capsule, it may contain in addition to materials of the above type a liquid carrier such as a fatty oil. Various other materials may be present as coatings or to otherwise enhance the pharmaceutical elegance of the preparation. For instance, tablets may be coated with shellac, sugar or the like. A syrup of elixir may contain the active compound, sucrose as a sweetening agent, methyl and propyl parabens as preservatives, a dye, and a flavoring such as cherry or orange flavor.

Sterile compositions for injection can be formulated according to conventional pharmaceutical practice by dissolving or suspending the active substance in a conventional vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The 2,4-dioxo-4-substituted-1-butanoic acid compounds of Formula I may be prepared in accordance with a reaction scheme which may be illustrated as follows:

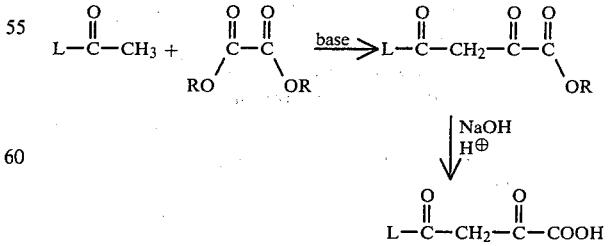

where R is $C_{1-4}$ alkyl, preferably methyl or ethyl; and L has the same meaning as above.

The methyl ketone starting materials are prepared by acetylation of a compound L-H with acetyl chloride or acetic anhydride and a Lewis acid catalyst under conventional Friedel-Crafts conditions, or by other routes well known in the art.

The first step of the reaction, in which the substituted methyl ketone is reacted with $C_{1-4}$ alkyl oxalate, can be carried out in solvents such as benzene, tetrahydrofuran, dimethylformamide, dioxane, and the like, in the presence of strong bases such as sodium or potassium methoxides, ethoxides, or butoxides at temperatures from 0° to 50° C.

Following are examples which illustrate the preparation of representative compounds and compositions falling within the present invention, although no limitation is thereby intended.

EXAMPLE 1

4-(4-Cyclohexylphenyl)-2,4-dioxo-1-butanoic acid

Step A

4-Cyclohexyl acetophenone

There was introduced to a 1 liter 3-neck flask under nitrogen atmosphere 41.7 g (0.312 Mol) of aluminum chloride, followed by 250 ml of dichloromethane. The mixture was cooled in an ice bath and 39.3 g (0.5 Mol) of acetyl chloride was added dropwise. This was followed by dropwise addition of 40.0 g of cyclohexylbenzene in 100 ml of dichloromethane. Fifteen minutes after addition was complete, 25 g of ice and then 25 ml of water were added to the reaction mixture, whereupon a thick white solid formed. The dichloromethane was decanted and washed with water, then three times with 30 ml of saturated saline solution, after which it was dried overnight over magnesium sulfate. After filtration, the remaining dichloromethane was evaporated, and the residue crystallized on cooling. The residue was recrystallized from petroleum ether to give 28.1 g. of product, m.p. 65°–67° C. Analysis:

Calc'd: %C, 83.12; %H, 8.97; %O, 7.91. Found: %C, 83.49; %H, 9.07.

Step B

Methyl 4-(4-cyclohexylphenyl)-2,4-dioxo-1-butanoate

To 22 ml of dry benzene there was added, under nitrogen atmosphere, 1.68 g (31.2 mMol) of sodium methoxide. There was then slowly added with stirring a solution of 6.06 g (30 mMol) of the 4-cyclohexyl acetophenone prepared in Step A above and 3.54 g (30 mMol) of freshly recrystallized dimethyl oxalate in 40 ml of benzene. The reaction mixture was cooled and soon after addition a yellow crystalline precipitate formed. The reaction mixture was allowed to warm to room temperature and stirred for an additional hour. There was then added 75 ml of ether and 24 ml of 2 N hydrochloric acid with 6 ml of water. The mixture was shaken for about 15 minutes, until all of the solid dissolved. The organic layer was then separated, washed with a small amount of water, and dried over magnesium sulfate. The solvent was then evaporated, the residue partially crystallized on cooling, and then crystallized from 3:1 petroleum ether:benzene. After cooling, 3.33 g of yellow solid product, m.p. 96°–98° C., was filtered off.

Step C 4-(4-Cyclohexylphenyl)-2,4-dioxo-1-butanoic acid

In 20 ml of ethanol and 2.4 ml of dioxane there was suspended 1.15 g (4 mMol) of the ester product prepared in Step B above. There was then added 3 ml of 2 N potassium hydroxide, whereupon a precipitate formed. The reaction mixture was stirred overnight at room temperature. The mixture was evaporated to dryness, an then water was added, whereupon most of the solid dissolved. The mixture was then made acidic to pH 1.0 using 6 N hydrochloric acid. A white solid was obtained which was filtered off, washed with water and dried. The solid was crystallized from benzene to give product, m.p. 140°–142° C. Analysis:

Calc'd: %C, 70.05; %H, 6.61. Found: %C, 69.60; %H, 6.81.

EXAMPLE 2

2,4-Dioxo-4-(4-nonylphenyl)-1-butanoic acid

Step A

Methyl 2,4-dioxo-4-(4-nonylphenyl)-1-butanoate

In 15 ml of dry benzene there was suspended 1.124 g (20.8 mMol) of sodium methoxide, and the mixture was cooled. The reaction was carried out under nitrogen. To the reaction mixture there was then added 4.92 g (20 mMol) of 4-nonylacetophenone and 2.36 g (20 mMol) of dimethyl oxalate in 25 ml of benzene. The reaction mixture was stirred at room temperature for 1 hour, and then 50 ml of ether, 16 ml of 2 N hydrochloric acid, and 4 ml of water were added, followed by stirring for an additional hour. The ether layer was separated and the aqueous layer was washed three times with 15 ml of ether. The ether layers were combined and washed five times with 10 ml of water, and three times with 10 ml of saturated sodium chloride solution. The ether layer was then dried over magnesium sulfate and evaporated, giving 6.86 g of crude product. This was crystallized from boiling petroleum ether, giving 3.45 g in the first crop, m.p. 55°–57° C.; and 1.1 g in the second crop, m.p. 52°–53.5° C. Analysis:

Calc'd: %C, 72.26; %H, 8.49; Found: %C, 72.26; %H, 8.81.

Step B 2,4-Dioxo-4-(4-nonylphenyl)-1-butanoic acid

There are dissolved in 45 ml of ethanol and 5.4 ml of dioxane 2.92 g (8.9 mMol) of the ester product of Step A above. To this solution 6.75 ml of 2 N potassium hydroxide was added, whereupon a precipitate formed. The reaction mixture was stirred at room temperature for 4 hours, then evaporated to dryness, dissolved in water, and extracted with ether. The aqueous layer was then acidified to pH 1 using 2 N hydrochloric acid; and the product was extracted into ethyl acetate, after which it was dried and evaporated, to yield 1.8 g. The crude product was crystallized from benzene, giving 480 mg in the first crop, m.p. 93°–94° C.; and 320 mg in the second crop, m.p. 90°–91° C. Analysis:

Calc'd: %C, 71.67; %H, 8.23; Found: %C, 71.45; %H, 8.61.

EXAMPLE 3

4-[(4'-bromo-1,1'-biphenyl)-4-yl]-2,4-dioxo-1-butanoic acid

Step A

1-Acetyl-4'-bromo-biphenyl

In a reaction flask under nitrogen atmosphere there was placed 26.6 g (0.2 Mol) of aluminum chloride, which was then covered with 150 ml of dichloromethane. There was then added dropwise 15.6 g (0.2 Mol) of acetyl chloride in 200 ml of dichloromethane, while cooling the reaction mixture. To this was added dropwise 23.3 g (0.1 Mol) of 4-bromobiphenyl in 200 ml of dichloromethane. The reaction mixture was allowed to warm to room temperature, and it was then heated to reflux for 4 hours, after which it was left at room temperature overnight under nitrogen atmosphere. There was then added 50 g of ice and the aqueous layer was separated. The organic layer was washed twice with 50 ml of saturated sodium chloride solution, then dried over magnesium sulfate and evaporated. The crude product was crystallized from 3:1 petroleum ether:benzene to give 16.9 g in the first crop, m.p. 126°–128° C.; and 3.9 g in the second crop.

Step B

Methyl 4-[(4'-bromo-1,1'-biphenyl)-4-yl]-2,4-dioxo-1-butanoate

In a reaction flask under nitrogen atmosphere there was placed 1.4 g (25 mMol) of sodium methoxide and covered with 20 ml of dry benzene. There was then added dropwise a solution of 5.5 g (20 mMol) of the ketone product prepared in Step A above in 50 ml of benzene, and 2.36 g (20 mMol) of dimethyloxalate in 40 ml of benzene. A thick yellow solid was obtained, and the reaction mixture was stirred ½ hour in an ice bath, then 2 hours at room temperature. There was then added 70 ml of ether and 16 ml of 2 N hydrochloric acid with 4 ml of water. Ethyl acetate was then added, whereupon the solid dissolved. The organic layer was separated, washed with water, dried, and evaporated, to give 6.3 g of crude product. The product was crystalized from acetonitrile to give 3.42 g in the first crop, m.p. 130°–133° C. Analysis:

Calc'd: %C, 56.53; %H, 3.63; %Br, 22.12; Found: %C, 56.22; %H, 3.62; %Br, 22.39.

Step C

4[(4'-Bromo-1,1'-biphenyl)-4-yl]-2,4-dioxo-1-butanoic acid

In 20 ml of ethanol and 2.4 ml of dioxane there was suspended 1.44 g (4 mMol) of the ester product prepared in Step B above, to which there was then added 3 ml of 2 N potassium hydroxide. A solid precipitate formed, and the reaction mixture was stirred at room temperature overnight, after which it was evaporated to dryness and water was then added. The solid was filtered off and suspended in the water solution, which was then made acidic (pH 1) using 6 N hydrochloric acid and extracted with methylene chloride. The extract was evaporated to give 0.51 g of a slightly yellow solid, m.p. 197°–200° C., which was recrystallized from acetonitrile, m.p. 201°–202° C. Analysis:

Calc'd: %C, 55,35; %H, 3.19; %Br, 23.02; Found: %C, 55,33; %H, 3.25; %Br, 23.29.

EXAMPLE 4

4-[4-(1,2,3,4-tetrahydro-1-naphthalenyl)phenyl]-2,4-dioxo-1-butanoic acid

Step A

Methyl 4-[4-(1,2,3,4-tetrahydro-1-naphthalenyl)phenyl]-2,4-dioxo-4-butanoic acid Into a reaction flask under nitrogen atmosphere was placed 0.648 g (0.012 Mol) of sodium methoxide and covered with 15 ml of dry benzene. The mixture was cooled in an ice bath, and there was then added dropwise a mixture of 20 ml (0.008 Mol) of 4-(1,2,3,4-tetrahydro-1-naphthalenyl)acetophenone in 15 ml of benzene and 1.416 g (0.012 Mol) of dimethyl oxalate in 15 ml of benzene. The ice bath was removed, and the reaction mixture was stirred at room temperature for 2 hours. Since thin layer chromatography showed little product, more sodium methoxide (0.432 g, 0.008 Mol) and dimethyl oxalate (0.944 g, 0.008 Mol) were added, and the reaction mixture was stirred at room temperature for 1.5 hours. There was then added 25 ml of 1 N hydrochloric acid and ethyl acetate. The mixture was stirred for 10 minutes, then separated, and the aqueous layer was extracted with more ethyl acetate. The organic layers were combined and washed twice with water, then dried over magnesium sulfate and evaporated to yield 2.82 g of crude product. Recrystallization from diisopropyl ether gave 0.84 g of product, m.p. 103°–105° C. Analysis:

Calc'd: %C, 74.98; %H, 5.99; Found: %C, 74.92; %H, 6.27.

Step B

4-[4-(1,2,3,4-tetrahydro-1-naphthalenyl)phenyl]-2,4-dioxo-1-butanoic acid hemihydrate There was dissolved in 10 ml of tetrahydrofuran 672 mg of the ester product prepared in Step A above, and then 5 ml of 1 N sodium hydroxide was added. The reaction mixture was stirred for an additional ½ hour, and then made acidic using 2 N hydrochloric acid. The aqueous layer was separated and extracted with ether. The combined organic layers were washed with saturated sodium chloride solution, dried over magnesium sulfate, and evaporated. To the oily residue there was added benzene and petroleum ether; and a solid was then obtained which was filtered, washed with petroleum ether, and dried under vacuum. The crude product (480 mg) was crystallized from benzene and dried under high vacuum, m.p. 117°–120° C.

Analysis for $C_{20}H_{18}O_4 \cdot \frac{1}{2}H_2O$: Calc'd: %C, 72.49; %H, 5.77; Found: %C, 72.67; %H, 5.95.

EXAMPLE 5

4-[4-(3,4-Dichlorophenylmethyl)phenyl]-2,4-dioxo-1-butanoic acid

Step A 4-(3,4-Dichlorophenylmethyl)acetophenone

There was placed in a reaction flask 56.9 g (0.24 Mol) of 3,4-dichlorodiphenylmethane, which was then covered with 225 ml of dichloromethane. Then, 20.72 g (0.264 Mol) of acetyl chloride was added, and the reaction flask was placed in an ice bath. The reaction was carried out under nitrogen atmosphere. There was then added 39.9 g (0.3 Mol) of aluminum chloride in 2 g portions. The reaction mixture was allowed to stand for 1 hour, after which an additional 1.9 g of acetyl chloride was added and the reaction mixture was stirred. It was allowed to warm to room temperature and was worked up after 1 hour of stirring. Crushed ice was added to the reaction mixture, and then the dichloromethane layer was separated, washed with water and a little hydrochloric acid, twice with plain water, and twice with saturated sodium chloride solution. The dichloromethane layer was then separated, dried over magnesium sulfate, and evaporated. The residue crystallized overnight on refrigeration, giving 46.22 g of crude product. Of this, 2 g were recrystallized from 8 ml of diisopropyl ether and 2 ml of petroleum ether. About 500 mg were obtained in the first crop, m.p. 38°–40° C. Analysis:

Calc'd: %C, 64.53; %H, 4.33; %Cl, 25.39 Found: %C, 64.52; %H, 4.41; %Cl, 25.12.

Step B

Methyl 4-[4-(3,4-dichlorophenylmethyl)phenyl]-2,4-dioxo-1-butanoate

Into a reaction flask there was placed 3.24 g (60 mMol) of sodium methoxide, which was covered with 40 ml of benzene. The reaction flask was under a nitrogen atmosphere and was placed in an ice bath. There was then added a solution of 8.37 g (30 mMol) of the acetophenone product prepared in Step A above and 7.08 g (60 mMol) of dimethyl oxalate in 80 ml of benzene. After 2 hours stirring, an additional 3.5 g (30 mMol) of dimethyl oxalate and 1.62 g (30 mMol) of sodium methoxide was added. The reaction mixture was then stirred at room temperature overnight, whereupon a yellow solid precipitated. There was added 45 ml of 2 N hydrochloric acid and 100 ml of water and the reaction mixture was stirred for 10 minutes. The organic layer was separated, washed twice with 50 ml of water, twice with saturated sodium chloride solution, dried over magnesium sulfate, and evaporated. The residue was recrystallized from 150 ml of diisopropyl ether and 20 ml of benzene to give 3.95 g in the first crop, m.p. 104°–106° C.

Step C

4-[4-(3,4-Dichlorophenylmethyl)phenyl]-2,4-dioxo-1-butanoic acid

There was dissolved in 15 ml of tetrahydrofuran and 3.75 ml of 2 N sodium hydroxide 1.09 g (3 mMol) of the ester product prepared in Step B above; and the reaction mixture was stirred overnight at room temperature, whereupon a solid precipitated. Then, 4 ml of 2 N hydrochloric acid was added, and the mixture was stirred well. The tetrahydrofuran layer was then separated, and the aqueous layer was extracted twice with 20 ml of diethyl ether. The combined organic layers were dried and evaporated. The oily residue solidified on standing. The material was crystallized from carbon tetrachloride, whereupon a yellow solid was obtained (370 mg), m.p. 133°–140° C. The material was crystallized again from carbon tetrachloride, m.p. 142°–144° C. Analysis:

Calc'd: %C, 58.14; %H, 3.44; %Cl, 20.19; Found: %C, 57.81; %H, 3.56; %Cl, 20.00.

EXAMPLE 6

Dry-filled capsules containing 50 mg. of Active Ingredient per Capsule

| Ingredient | Amount Per Capsule |
|---|---|
| 4-[(1,1'-biphenyl)-4-yl]-2,4-dioxo-1-butanoic acid | 50 mg. |
| Lactose | 149 mg. |
| Magnesium Stearate | 1 mg. |
| Capsule (Size No. 1) | 200 mg. |

The active ingredient is reduced to a No. 60 powder and then lactose and magnesium stearate are passed through a No. 60 bolting cloth onto the powder and the combined ingredients admixed for 10 minutes and then filled into a No. 1 dry gelatin capsule.

EXAMPLE 7

Glycolate Oxidase Enzyme Inhibition

The usefulness of the compounds of the present invention in treating urinary tract, especially renal, calcium oxalate lithiasis, is shown by the ability of those compounds to inhibit the glycolate oxidase enzyme. This inhibition was determined by observing the extent to which the test compound blocked the activity of the enzyme. The activity of the enzyme, in turn, was measured by following the rate of reduction of sodium 2,6-dichlorophenyl-indophenol by sodium glycolate in the presence of the enzyme. The enzyme was pig liver glycolate oxidase. The reaction was followed spectrophotometrically at 600 nm. The assay was conducted at 25° C. in a 0.10 M phosphate buffer, pH 7.0, containing 3 mM EDTA. Initial substrate concentrations were $5 \times 10^{-5}$ M of sodium 2,6-dichlorophenol and $2 \times 10^{-4}$ M of sodium glycolate. Reactions were initiated by the addition of enzyme. Initial rates during the period from 1 to 3 minutes after the addition of enzyme were recorded on a Beckman Acta M-VI spectrophotometer. One control was run simultaneously with three reactions, and all initial rates were adjusted to a common control rate. For further details of this procedure, see Randall et al., *J. Med. Chem.*, 22, 6,612 (1979).

The results obtained from this assay are illustrated below.

| Compound | $IC_{50}$ |
|---|---|
| 4-(4-cyclohexylphenyl)-2,4-dioxo-1-butanoic acid | $2.5 \times 10^{-6}$ M |
| 2,4-dioxo-4-(4-nonylphenyl)-1-butanoic acid | $6.7 \times 10^{-7}$ M |
| 4-[(4'-bromo-1,1'-biphenyl)-4-yl]-2,4-dioxo-1-butanoic acid | $7 \times 10^{-8}$ M |
| 2,4-dioxo-4-[4-(1,2,3,4-tetrahydro-1-naphthalanyl)phenyl]-1-butanoic acid | $2.1 \times 10^{-6}$ M |
| 4-[4-(3,4-dichlorophenylmethyl)phenyl]-2,4-dioxo-1-butanoic acid | $4.6 \times 10^{-7}$ M |

What is claimed is:

1. A compound of the formula:

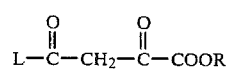

where

R is hydrogen or $C_{1-4}$ alkyl and

L is a lipophilic group consisting essentially of:

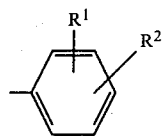 (1)

where $R^1$ and $R^2$ are each independently selected from the group consisting of (a) hydrogen; (b) $C_{4-12}$ straight or branched chain alkyl; (c) $C_{4-7}$ cycloalkyl; and (d) tetrahydronaphthyl; provided that $R^1$ and $R^2$ may not both be hydrogen; and when one of $R^1$ or $R^2$ is tetrahydronaphthyl, the other must be some other substituent; and that positions 2 and 6 of the substituted phenyl moiety may not be substituted; and

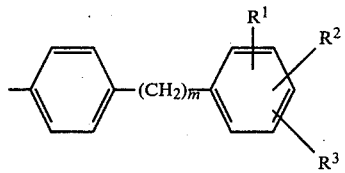 (2)

where $R^1$, and $R^2$ have the same meaning as above except tetrahydronaphthyl;

$R^3$ is bromine, chlorine, or fluorine;

m is 0 to 3;

or a pharmaceutically acceptable salt thereof.

2. A compound according to claim 1 wherein the compound is 4-(4-cyclohexylphenyl)-2,4-dioxo-1-butanoic acid.

3. A compound according to claim 1 wherein the compound is 2,4-dioxo-4-(4-nonylphenyl)-1-butanoic acid.

4. A compound according to claim 1 wherein the compound is 4-[(4'-bromo-1,1'-biphenyl)-4-yl]-2,4-diox-o-1-butanoic acid.

5. A compound according to claim 1 wherein the compound is 4-[4-(1,2,3,4-tetrahydro-1-naphthalenyl)-phenyl]-2,4-dioxo-1-butanoic acid hemihydrate.

6. A compound according to claim 1 wherein the compound is 4-[4-(3,4-dichlorophenylmethyl)phenyl]-2,4-dioxo-1-butanoic acid.

7. A method of treating or preventing the formation of calcium oxalate urinary tract lithiasis, especially kidney or bladder stones, which comprises administering to a patient with, or prone to, such disease a therapeutically effective amount of a compound of the formula:

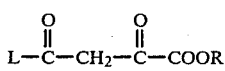 (I)

where

R is hydrogen or $C_{1-4}$ alkyl and

L is a lipophilic group consisting essentially of:

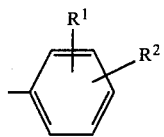 (1)

where $R^1$ and $R^2$ are each independently selected from the group consisting of (a) hydrogen; (b) $C_{4-12}$ straight or branched chain alkyl; (c) $C_{4-7}$ cycloalkyl; and (d) tetrahydronaphthyl; provided that $R^1$ and $R^2$ may not both be hydrogen; and when one of $R^1$ or $R^2$ is tetrahydronaphthyl, the other must be some other substituent; and that positions 2 and 6 of the substituted phenyl moiety may not be substituted; and

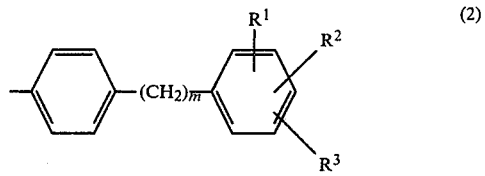 (2)

where $R^1$, and $R^2$ have the same meaning as above except tetrahydronaphthyl;

$R^3$ is bromine, chlorine, or fluorine;

m is 0 to 3;

or a pharmaceutically acceptable salt thereof.

8. A pharmaceutical composition for use in treating or preventing the formation of calcium oxalate urinary tract lithiasis, especially kidney or bladder stones, comprising a pharmaceutically acceptable carrier and a compound of the formula:

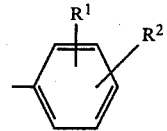 (1)

where

R is hydrogen or $C_{1-4}$ alkyl and

L is a lipophilic group consisting essentially of:

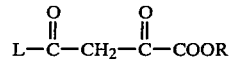 (I)

where $R^1$ and $R^2$ are each independently selected from the group consisting of (a) hydrogen; (b) $C_{4-12}$ straight or branched chain alkyl; (c) $C_{4-7}$ cycloalkyl; and (d) tetrahydronaphthyl; provided that $R^1$ and $R^2$ may not both be hydrogen; and when one of $R^1$ or $R^2$ is tetrahydronaphthyl, the other must be some other substituent; and that positions 2 and 6 of the substituted phenyl moiety may not be substituted; and

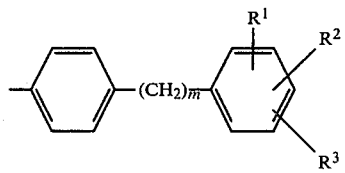 (2)

where $R^1$, and $R^2$ have the same meaning as above except tetrahydronaphthyl;

$R^3$ is bromine, chlorine, or fluorine;

m is 0 to 3;

or a pharmaceutically acceptable salt thereof.

* * * * *